US009249310B2

(12) United States Patent
Svensson

(10) Patent No.: US 9,249,310 B2
(45) Date of Patent: Feb. 2, 2016

(54) POLYSACCHARIDE CONTAINING COMPOSITION USEFUL IN FORMING PROTECTIVE FILM ON SURFACES SELECTED FROM CONCRETE, METAL, STONE, GLASS, WOOD, CLOTH, TISSUE, WEAVE AND PAPER

(75) Inventor: Sigfrid Svensson, Bryssel (BE)

(73) Assignee: LYCKEBY STARCH AB, Kristianstad (SE)

( * ) Notice: Subject to any disclaimer, the term of this patent is extended or adjusted under 35 U.S.C. 154(b) by 1255 days.

(21) Appl. No.: 12/998,756

(22) PCT Filed: Dec. 2, 2009

(86) PCT No.: PCT/SE2009/051363
§ 371 (c)(1),
(2), (4) Date: Jul. 26, 2011

(87) PCT Pub. No.: WO2010/064982
PCT Pub. Date: Jun. 10, 2010

(65) Prior Publication Data
US 2011/0275260 A1  Nov. 10, 2011

(30) Foreign Application Priority Data
Dec. 3, 2008 (SE) ...................................... 0802519

(51) Int. Cl.
| C09D 105/00 | (2006.01) |
| C09D 5/00 | (2006.01) |
| A01N 25/04 | (2006.01) |
| C04B 41/00 | (2006.01) |
| C04B 41/48 | (2006.01) |
| C04B 41/63 | (2006.01) |
| C08B 30/12 | (2006.01) |
| C08B 37/00 | (2006.01) |
| C08K 3/04 | (2006.01) |
| C08K 5/00 | (2006.01) |
| C08L 3/02 | (2006.01) |
| C08L 5/00 | (2006.01) |
| C08L 5/12 | (2006.01) |
| C09D 5/16 | (2006.01) |
| D21H 17/28 | (2006.01) |
| B05D 5/08 | (2006.01) |
| C04B 111/25 | (2006.01) |
| D21H 19/54 | (2006.01) |

(52) U.S. Cl.
CPC ............... *C09D 5/008* (2013.01); *A01N 25/04* (2013.01); *C04B 41/009* (2013.01); *C04B 41/4803* (2013.01); *C04B 41/63* (2013.01); *C08B 30/12* (2013.01); *C08B 37/0039* (2013.01); *C08B 37/0096* (2013.01); *C08K 3/04* (2013.01); *C08K 5/0008* (2013.01); *C08L 3/02* (2013.01); *C08L 5/00* (2013.01); *C08L 5/12* (2013.01); *C09D 5/1656* (2013.01); *C09D 105/00* (2013.01); *D21H 17/28* (2013.01); *B05D 5/08* (2013.01); *C04B 2111/25* (2013.01); *C08L 2205/02* (2013.01); *D21H 19/54* (2013.01); *Y10T 428/263* (2015.01); *Y10T 428/31641* (2015.04); *Y10T 428/31714* (2015.04); *Y10T 428/31844* (2015.04); *Y10T 428/31848* (2015.04); *Y10T 442/20* (2015.04)

(58) Field of Classification Search
CPC ....... A01N 25/04; A01N 37/40; A01N 53/00; C04B 41/009; C04B 41/4803; C04B 41/63; C04B 28/02; C04B 2111/25; C08B 30/12; C08B 37/0039; C08B 27/0096; C08K 3/04; C08K 5/0008; C08K 5/0058; C08K 5/053; C08L 3/02; C08L 5/00; C08L 5/12; C08L 2205/02; C09D 5/008; C09D 5/1656; C09D 105/00; D21H 17/28; D21H 19/54; B05D 5/08
See application file for complete search history.

(56) References Cited

U.S. PATENT DOCUMENTS

| 5,017,237 A | 5/1991 | Svensson |
| 5,093,485 A | 3/1992 | Svensson |
| 5,198,254 A | 3/1993 | Nisperos-Carriedo et al. |
| 5,376,391 A | 12/1994 | Nisperos-Carriedo et al. |
| 5,750,189 A | 5/1998 | Svensson |
| 5,948,545 A | 9/1999 | Svensson |

(Continued)

FOREIGN PATENT DOCUMENTS

| EP | 0365584 A1 | 5/1990 |
| EP | 0470871 A1 | 2/1992 |

(Continued)

OTHER PUBLICATIONS

Mitsuki et al, "Determiniation of molecular weight of agars and effect of the molecular weight on the glass transition.", J. Agric. Food Chem., (Feb. 1999) Abstract.*

(Continued)

*Primary Examiner* — David M Brunsman
(74) *Attorney, Agent, or Firm* — Harness, Dickey & Pierce, P.L.C.

(57) ABSTRACT

A polysaccharide composition for protection of surfaces comprising an aqueous solution of at least two components, the first component (A) being a high molecular weight polysaccharide or a mixture of high molecular weight polysaccharides having an average molecular weight Mw of at least 100 000, and being capable of forming a gel, and the second component (B) being a low molecular weight polysaccharide such as locust bean or guar gum or a mixture of low molecular weight polysaccharides having an average molecular weight Mw of 400-75 000, and being capable of inhibiting gel formation in said composition.

26 Claims, No Drawings

(56) References Cited

U.S. PATENT DOCUMENTS

| | | |
|---|---|---|
| 5,976,586 A | 11/1999 | Feller |
| 6,068,867 A | 5/2000 | Nussinovitch et al. |
| 7,060,742 B2 * | 6/2006 | Svensson .................. 524/55 |

FOREIGN PATENT DOCUMENTS

| | | |
|---|---|---|
| JP | 2006-160816 | 6/2006 |
| WO | WO-8810156 A1 | 12/1988 |
| WO | WO-8810284 A1 | 12/1988 |
| WO | WO-9217070 A1 | 10/1992 |
| WO | WO-9525604 A1 | 9/1995 |
| WO | WO-9525605 A1 | 9/1995 |
| WO | WO-9613984 A1 | 5/1996 |
| WO | WO-2004098287 A1 | 11/2004 |

OTHER PUBLICATIONS

International Search Report for PCT/US2009/051363, (Mar. 2010).

* cited by examiner

POLYSACCHARIDE CONTAINING COMPOSITION USEFUL IN FORMING PROTECTIVE FILM ON SURFACES SELECTED FROM CONCRETE, METAL, STONE, GLASS, WOOD, CLOTH, TISSUE, WEAVE AND PAPER

FIELD OF THE INVENTION

The present invention relates to compositions and methods for protecting surfaces from non-desired contamination and for facilitating removal of such contamination from the surfaces.

BACKGROUND

Protective films or coatings comprising polysaccharides are useful in many different applications, such as protection of all types of surfaces from so called graffiti, traffic pollution, bird droppings, etc.

In EP 0 365 584 B1 there is described a contamination removal process based on the use of a solution containing a polysaccharide and a solvent therefore for creating a protective coating on a surface. After being subjected to contamination, the surface can easily be freed from the contamination by treating the coated surface with a liquid, which is capable of re-dissolving the protective coating.

A number of polysaccharides, for example carrageenans and agar, when dissolved in water at an increased temperature form gels, at certain minimum concentrations when the solution is cooled to a lower temperature. It is known that this property may be used to produce polysaccharide films having an improved stability towards water. If a polysaccharide of the gelling type is used alone, the concentration thereof in solution has to be very low in order to obtain a solution thereof that can be applied to a substrate without difficulty, resulting in thin films. If, on the other hand, the concentration is increased to a level which will result in sufficient film thickness from a single application, then gelling will occur prior to application and the application by spraying or the like will constitute a severe problem.

U.S. Pat. No. 5,948,545 describes a method for protecting a surface from contamination and for facilitating removal thereof using a solution of at least a first polysaccharide and a second polysaccharide, wherein the second polysaccharide or the mixture of the first and second polysaccharide is capable of gel formation. The first polysaccharide is added to the solution to inhibit gel formation in order to allow a higher polysaccharide concentration in the solution while avoiding premature gel formation. A problem associated with the method of U.S. Pat. No. 5,948,545 is that the addition of polysaccharides in order to inhibit gel formation generally results in very high viscosity solutions, which impedes application onto substrates using conventional coating techniques, such as spraying.

Therefore, there is a demand for a new polysaccharide composition which produces protective coatings of sufficient thickness, but without the drawbacks of high viscosity and premature gel formation associated with the prior art methods.

DESCRIPTION OF THE INVENTION

It is an object of the present invention to alleviate at least some of the problems associated with the prior art techniques.

In particular, it is an object of the present invention to provide a composition which allows application by conventional coating methods of a polysaccharide film having a sufficient thickness and stability towards water at room temperature in a single application.

It is another object of the invention to provide a polysaccharide film or coating which may easily be removed from a surface onto which it has been applied.

Yet another object of the present disclosure is to provide a composition, which in combination with insecticides or fungicides may be used for the protection of plant parts such as stems, leaves and fruits.

In order for a protective polysaccharide film to be effective, the thickness of the film has to be sufficient. Sufficient film thickness can generally be achieved in two ways. The first way is by repeated application of the solution to the surface resulting successive build-up of a sufficient thickness. Such a method carries the obvious disadvantage of having to apply the solution several times and allowing the film to dry between the applications, making the coating procedure time consuming and expensive. The second way is by a single application of a solution having a sufficient dry weight of polysaccharide to provide a sufficiently thick film. This method, although attractive, is not feasible using the polysaccharide solutions described in the prior art. The reason for this is that the required increase in the dry weight of polysaccharide in the prior art solutions will result in an increase in the viscosity of the solutions, such that coating of the solutions using conventional coating techniques will be very difficult.

The above mentioned objects, as well as other objects that will be apparent to a person skilled in the art when presented with the present disclosure, are accomplished by the different aspects of the present invention.

In a first aspect thereof, the present invention provides a polysaccharide composition for protection of surfaces comprising an aqueous solution of at least two components, the first component (A) being a high molecular weight polysaccharide or a mixture of high molecular weight polysaccharides having an average molecular weight $M_w$ of at least 100 000, and being capable of forming a gel, and the second component (B) being a low molecular weight polysaccharide or a mixture of low molecular weight polysaccharides having an average molecular weight $M_w$ of 400-75 000, and being capable of inhibiting gel formation in said composition, wherein the weight ratio between A and B is in the range of from 5:1 to 1:50 based on polysaccharide dry weight, and the total concentration of A+B in the composition is in the range of 0.1-30% (w/v) based on polysaccharide dry weight.

The present invention makes use of the advantage of gel formation as an intermediary step in the process of obtaining a water resistant protective polysaccharide coating or film. More specifically, the invention is based on the inventive realization that the gel formation of high molecular weight polysaccharides or mixtures of different high molecular weight polysaccharides can be inhibited by the addition of low molecular weight polysaccharides or oligosaccharides.

If a polysaccharide of the gel forming type is used alone in solution, the concentration thereof has to be very low to obtain a solution that can be applied to a substrate surface without difficulty due to high viscosity and/or premature gel formation. If the concentration of the polysaccharide is increased to a level which would result in sufficient film thickness when the solution is applied to a substrate, then gel formation will occur and the application by spraying or the like will constitute a severe problem. In other words, a problem to be solved by the invention can be said to reside in finding new techniques, whereby it is possible to make use of the advantages associated with gel formation as an intermediate stage in the formation of polysaccharide coatings, while at the same time providing for a concentration of polysaccharides in the coating solution resulting in a protective film of sufficient thickness. The present invention solves this problem and thereby constitutes a significant advance in the art.

When solvent is evaporated from a solution comprising a polysaccharide capable of forming a gel, the concentration of polysaccharide in the solution will eventually reach a critical point at which gel formation occurs. This critical point is important in the preparation and use of polysaccharide coatings. The gel formation should preferably occur during the evaporation of the remaining solvent in the coating before a solid film is formed on a substrate. If gel formation occurs too soon, i.e. before sufficient wetting of the substrate, the properties of the protective film, in terms of coverage and adhesion, will be adversely affected. If gel formation does not occur before the film is formed, the water resistance and mechanical properties of the protective film will be adversely affected. The present invention provides for the timing of gel formation in the film to be tailored by varying the weight ratio between the different components to optimize the properties in the finished protective film.

The composition and methods of the present invention have several surprising advantages over the compositions and methods of the prior art.

A significant advantage of the present invention as compared to the compositions and methods of the prior art, is that it provides for obtaining a thick film with one application only without compromising the stability of the film towards water at room temperature.

The composition of the present invention allows a high total concentration of polysaccharide in solution without the disadvantage of very high viscosity of the solution. The low molecular weight polysaccharides or oligosaccharides of the present invention have the advantage of a significantly lower contribution to the total viscosity of the solution as compared to a corresponding amount of high molecular weight polysaccharide. In other words, a relatively high amount of low molecular weight polysaccharide may be added to the solution with only a relatively low increase of the viscosity. More specifically, the present invention may allow total polysaccharide concentrations of up to 30% (w/v) based on dry weight of polysaccharide, as compared to prior art high molecular weight polysaccharide solutions which are generally limited to concentrations below 3-4% in order to maintain an acceptable viscosity in the solution.

The present inventor has surprisingly found that a high amount of a low molecular weight polysaccharide may be added to the composition without impairing the properties of the solid protective film in terms of mechanical strength and stability towards water.

The composition of the present invention comprises an aqueous solution of at least one high molecular weight polysaccharide being capable of forming a gel, and at least one low molecular weight polysaccharide being capable of inhibiting gel formation of said high molecular weight polysaccharide. The polysaccharides may be partially or completely dissolved in the aqueous solution. Preferably the polysaccharides are completely or substantially completely dissolved in the aqueous solution. In an embodiment, the composition consists of said solution.

The composition of the invention comprises as component A at least one high molecular weight polysaccharide capable of forming a gel, either by itself or by interaction with other components in the composition.

The average molecular weight $M_w$ of the high molecular weight polysaccharide capable of forming a gel is preferably 100 000 or higher, such as 250 000 or higher or 500 000 or higher. The average molecular weight $M_w$ may for example be in the range of 100 000-5 000 000 or in the range of 100 000-5 00 000 or in the range of 500 000-5 000 000. In an embodiment, wherein the average molecular weight $M_w$ is 100 000 or higher, or 250 000 or higher, or 500 000 or higher, preferably at least 75% of the polysaccharide molecules should have a molecular weight above that value. In an embodiment, wherein the average molecular weight $M_w$ is in the range of 100 000-5 000 000 or in the range of 500 000-5 000 000, preferably at least 75% of the polysaccharides should have a molecular weight within the respective range.

Gel formation may occur by a number of different mechanisms, but the exact mechanism of the gel formation is not of essence to the present invention. Gel formation also depends on temperature and concentration of the polysaccharide solution.

The skilled person will recognize which polysaccharides and mixtures of different polysaccharides that may be subject to gel formation.

The composition of the invention may for example comprise, as component A, one high molecular weight polysaccharide capable of forming a gel by itself.

In an embodiment, the high molecular weight polysaccharide capable of forming a gel, i.e. component A, is selected from the group consisting of algal, microbial and plant derived polysaccharides or mixtures thereof.

In an embodiment, the high molecular weight polysaccharide capable of forming a gel, i.e. component A, is selected from the group consisting of, agar, carrageenans, gellan gum, pectins or mixtures thereof.

In an embodiment, the high molecular weight polysaccharide capable of forming a gel, i.e. component A, is agar.

The composition of the invention may as component A also comprise two or more different high molecular weight polysaccharides, wherein one of the polysaccharides is incapable of forming a gel by itself, but wherein a combination of the two or more polysaccharides is capable of forming a gel together. Examples of such combinations suitable for use with the present invention include a mixture of agar with guar gum, locust bean gum and/or xanthan gum.

In an embodiment, component A comprises a mixture of agar with guar gum, locust bean gum and/or xanthan gum. In another embodiment, component A comprises a mixture of agar with guar gum and/or locust bean gum.

The composition of the invention may as component A also comprise two different high molecular weight polysaccharides, wherein both of said polysaccharides are incapable of forming a gel by themselves, but wherein a combination of the two polysaccharides is capable of forming a gel together. An example of such a combination suitable for use with the present invention is the combination of xanthan gum with guar gum or locust bean gum. Such a combination may also include the case wherein one of the polysaccharides is a gel forming polysaccharide present in a concentration which is too low for gel formation to occur, and a second polysaccharide is a non-gel forming polysaccharide, and wherein the mixture of the two polysaccharides may form a gel together. Examples of such combinations of polysaccharides wherein each of the polysaccharides would not form a gel by themselves, but wherein the mixture forms a gel include, but are not limited to, a mixture of agar and guar gum or locust bean gum, wherein agar is present at a concentration, such as 0.05% (w/v) or less, at which it would not form a gel by itself at room temperature. The gelling concentration for different gel forming polysaccharides is generally well known or easily accessible to a person skilled in the art.

The composition of the invention comprises as component B at least one low molecular weight polysaccharide capable of inhibiting the formation of a gel of the composition comprising component A, either by interaction with component A or by interaction with other components in the composition. As will be evident below, component B prevents gel formation of the composition comprising component A prior to application onto a substrate surface. When the composition is applied onto a substrate surface and is allowed to dry, a film will be formed from the composition via at least partial gel formation.

The average molecular weight $M_w$ of the low molecular weight polysaccharide(s) of component B is generally within a range of 400-75 000, preferably within a range of 400-60000 or 400-50 000, and preferably at least 75% or 90% of the polysaccharides should have a molecular weight within said range. A lower average molecular weight $M_w$ than 400 may lead to a high portion of low molecular species which are not bound strongly enough within the formed film and may easily be washed out, or diffuse out, of the film. A molecular weight $M_w$ higher than 75 000 may not give the advantage of low viscosity in solution. Therefore, in an embodiment, the average molecular weight $M_w$ of the low molecular weight polysaccharide(s) of component B is preferably within a range of 400-50 000, and preferably at least 75% of the polysaccharides should have a molecular weight within said range. In another embodiment, the average molecular weight $M_w$ of the low molecular weight polysaccharide(s) of component B is preferably within a range of 400-25 000, and preferably at least 75% of the polysaccharides should have a molecular weight within said range.

Examples of polysaccharides suitable for use in the low molecular weight component of the inventive composition include, but are not limited to, low molecular weight species of all the different polysaccharides mentioned above in relation to the high molecular weight polysaccharides. In an embodiment, the low molecular weight polysaccharide is selected from the group consisting of low molecular weight agar, carrageenans, gellan gum, pectins, guar gum, locust bean gum, xanthan gum and mixtures thereof. In an embodiment, the low molecular weight polysaccharide is selected from the group consisting of low molecular weight agar, guar gum, locust bean gum, xanthan gum and mixtures thereof. In an embodiment, the low molecular weight polysaccharide is low molecular weight guar gum. In another embodiment, the low molecular weight polysaccharide is low molecular weight locust bean gum.

Low molecular weight polysaccharides suitable for use with the present invention may be obtained by a number of different methods. In a preferred embodiment, the low molecular weight component of the inventive composition comprises a hydrolysate of a higher molecular weight polysaccharide. A polysaccharide hydrolysate is a product from hydrolytic degradation of a polysaccharide resulting in cleavage of bonds connecting the polysaccharide units. Hydrolysis may be effected by a number of different methods, for example by acid or base hydrolysis, or by enzymatic hydrolysis. Hydrolysis allows the preparation of a polysaccharide having a desired average molecular weight $M_w$. Hydrolysis may also be combined with a method of separating low molecular weight species from the mixture formed on hydrolysis, such as for example dialysis, or gel filtration. Hydrolysis and separation of low molecular weight species allows the molecular weight distribution and the average molecular weight $M_w$ to be tailored within a wide range.

In an embodiment, component A and component B are different polysaccharides, e.g. component A is agar and component B is a guar gum hydrolysate. In another embodiment, component A and component B are the same type of polysaccharide but with different molecular weights. If this is the case, the high molecular weight polysaccharide should not be starch.

In a specific embodiment, component A comprises a high molecular weight polysaccharide capable of forming a gel, e.g. agar, and component B comprises a low molecular weight species of the polysaccharide of component B, e.g. an agar hydrolysate, capable of inhibiting gel formation in the composition.

Inhibition of gel formation may occur by a number of different mechanisms, such as for example sterical hindrance or competitive inhibition, but the exact mechanism of the inhibition of gel formation is not of essence to the present invention. Generally the degree of inhibition increases with increasing concentration of the low molecular weight polysaccharide relative to the concentration of the high molecular weight polysaccharide. If the relative concentration of the low molecular weight polysaccharide is too low, gel formation may occur too early and/or the viscosity of the composition becomes to high. If the relative concentration of the low molecular weight polysaccharide is too high, the stability of the resulting protective film towards water may be negatively affected. The weight ratio between low and high molecular weight polysaccharide should therefore be selected within a range which does not give premature gel formation, and which provides a protective film which is stable towards water at room temperature.

The weight ratio between the high and low molecular weight polysaccharides required for each specific composition may easily be determined by routine experimentation.

The weight ratio between A and B may preferably be below 5:1 based on polysaccharide dry weight, such as below 2:1 or 1:1, and preferably above 1:50, such as above 1:40, 1:30, 1:20, 1:10, 1:5 or 1:2.

In an embodiment, the weight ratio between A and B is in the range of from 5:1 to 1:20 based on polysaccharide dry weight. In another embodiment, the weight ratio between A and B is in the range of from 2:1 to 1:20 based on polysaccharide dry weight. In yet another embodiment, the weight ratio between A and B is in the range of from 2:1 to 1:10 based on polysaccharide dry weight. In another embodiment, the weight ratio between A and B is in the range of from 2:1 to 1:5 based on polysaccharide dry weight.

The total concentration of polysaccharide, i.e. low and high molecular weight polysaccharide, in the inventive composition will affect the thickness of a film formed by the composition. The higher the concentration, the thicker the protective film. The total concentration of polysaccharide in the solution should preferably selected such that the viscosity of the solution allows application of the solution to a substrate using conventional coating methods, such as spraying, while resulting in the formation of a polysaccharide protective film having a sufficient thickness.

The total concentration of polysaccharide, i.e. component A plus component B, in the inventive composition is preferably at least 0.1% (w/v) based on dry weight of polysaccharide, such as at least 0.5%, 1%, 2%, 5%, 10% or 20%, and the total concentration of polysaccharide, i.e. component A plus component B, in the inventive composition is preferably not higher than 30% (w/v) based on dry weight of polysaccharide, such as not higher than 20%, 10% or 5%.

The total concentration of polysaccharide, i.e. component A plus component B, in the inventive composition may preferably be in the range of 0.1-30% (w/v) based on dry weight of polysaccharide, more preferably in the range of 1-20%

(w/v) or 1-10% (w/v) based on dry weight of polysaccharide. The use of a low molecular weight polysaccharide according to the present invention allows for the use of higher polysaccharide content in solutions as compared to compositions comprising mainly high molecular weight polysaccharides. Prior art compositions are generally limited to a polysaccharide concentration of less than about 2% (w/v) based on dry weight of polysaccharide in order to avoid problems with high viscosity or premature gel formation. Thus, in an embodiment of the composition of the invention the total concentration of polysaccharide is in the range of 2-20% (w/v) based on dry weight of polysaccharide, more preferably 5-20% or 5-10% (w/v) based on dry weight of polysaccharide.

The concentration in the composition of component A, i.e. the high molecular weight polysaccharide or mixture of polysaccharides capable of forming a gel, should preferably be sufficiently high to allow formation of a gel when the water in the composition evaporates. The concentration in the composition of component A, i.e. the high molecular weight polysaccharide or mixture of polysaccharides capable of forming a gel, should also preferably be sufficiently low to allow inhibition of the gel formation by addition of a low molecular weight polysaccharide according to the invention. The concentration of the high molecular weight polysaccharide or mixture of polysaccharides capable of forming a gel may generally be at least 0.01% (w/v) based on dry weight of polysaccharide, such as at least 0.1%, 0.5%, 1%, or 5%. The concentration of the high molecular weight polysaccharide or mixture of polysaccharides capable of forming a gel may generally be below 10% (w/v) based on dry weight of polysaccharide, such as below 5% or below 2% in order to keep the viscosity down.

In an embodiment, the concentration of the high molecular weight polysaccharide or mixture of polysaccharides capable of forming a gel may be within a range of 0.01-10% (w/v) based on dry weight of polysaccharide. In an embodiment, the concentration of the high molecular weight polysaccharide or mixture of polysaccharides is in the range of 0.05-5% (w/v) based on dry weight of polysaccharide. In an embodiment, the concentration of the high molecular weight polysaccharide or mixture of polysaccharides is in the range of 0.1-2% (w/v) based on dry weight of polysaccharide.

The concentration in the composition of component B, i.e. the low molecular weight polysaccharide or mixture of polysaccharides capable of inhibiting the formation of a gel of the composition, either by interaction with component A or by interaction with other components in the composition should preferably be sufficiently high to obtain a desired inhibition of gel formation in the composition as well as to obtain a sufficiently thick protective film when the composition is applied to a substrate and allowed to dry, and sufficiently low to not completely inhibit gel formation so that no gel is formed. The concentration of component B, i.e. the low molecular weight polysaccharide or mixture of polysaccharides capable of inhibiting the formation of a gel in the composition may generally be at least 0.1% (w/v) based on dry weight of polysaccharide, such as at least 0.5%, 1%, 5%, 10% or 20%.

In an embodiment, the concentration of the low molecular weight polysaccharide or mixture of polysaccharides is in the range of 0.1-30% (w/v) based on dry weight of polysaccharide. In an embodiment, the concentration of the low molecular weight polysaccharide or mixture of polysaccharides is in the range of 1-20% (w/v) based on dry weight of polysaccharide. In an embodiment, the concentration of the high molecular weight polysaccharide or mixture of polysaccharides is in the range of 5-20% (w/v) based on dry weight of polysaccharide.

The composition of the invention may further comprise additives for improving the properties of the composition and of the protective films formed thereof.

The composition of the invention may further comprise as component C additional high molecular weight polysaccharides, each of which may or may not be capable of gel formation, provided that component A as a whole is still capable of forming a gel. The additional high molecular weight polysaccharides of component C provide an advantage in reduced permeability of the protective film. Component C may be removed from the composition without the composition losing its capability of gel formation. The polysaccharide(s) of component C are preferably different from those of components A and B. The concentration of component C is preferably such that it does not impart excessive viscosity to the composition, making the composition difficult to apply by conventional means, such as e.g. by spraying. The concentration of component C may generally be in the range of 0.01-10% (w/v) although higher or lower concentrations may be useful in specific embodiments. Examples of such polysaccharides include, but are not limited to, algal, microbial and plant derived polysaccharides, celluloses and derivatives thereof, starches and derivatives thereof. In an embodiment, an additional high molecular weight polysaccharide is selected from the group consisting of starch, a starch derivative, cellulose, and a cellulose derivative. In a more specific embodiment, the polysaccharide composition of the present invention, further comprises a third component (C), being a high molecular weight polysaccharide or a mixture of high molecular weight polysaccharides selected from the group consisting of starch, a starch derivative, cellulose and a cellulose derivative, wherein the total concentration of A+B+C in the composition is in the range of 0.1-30% (w/v) based on polysaccharide dry weight.

In an embodiment, the composition further comprises an anti-foaming agent. The addition of an anti-foaming agent is particularly advantageous in compositions comprising high concentrations of polysaccharides, since such compositions result in relatively thick films when applied to substrates. Bubbles remaining in the film when the solvent evaporates may lead to the formation of pin-holes in the solid film. Pinholes increase the permeability of the film to contamination. This problem is accentuated when the film is applied in a single application. The addition of an anti-foaming agent reduces pin-hole formation in thick polysaccharide films. Examples include n-octanol or similar higher aliphatic alcohols, although any suitable an anti-foaming agent may be used.

In an embodiment, the composition further comprises a plasticizer. Plasticizers help make the resulting film flexible. This is important in order to eliminate the formation of cracks in the film during the drying process. Cracks increase the permeability of the film to contamination. The addition of a plasticizer is particularly advantageous in compositions comprising high concentrations of polysaccharides, since such compositions result in relatively thick films that may be prone to crack formation during drying. Examples include glycerol or polyglycerols, although any suitable plasticizer may be used.

In an embodiment, the composition further comprises a surfactant. Surfactants reduce the surface tension of the composition and facilitates spreading of the composition on a substrate, and the filling of pores present in the substrate. A person skilled in the art may select a surfactant suitable for use with the present invention.

In an embodiment, the composition further comprises an additive for preventing lump formation of the polysaccharides when they are dissolved. The lump preventing additive may for example be ethanol present at a concentration of 10% or less.

In an embodiment, the composition is preferably provided with a pH buffer for the purpose of counteracting changes in the pH of the film formed independent of exterior influence. This is suitable particularly to withstand the influence of environmental conditions, such as acid rain, bird droppings, and other conditions involving acid or basic pH.

In an embodiment, the composition further comprises an antimicrobial agent and/or a preservative. An antimicrobial agent may reduce decay of the polysaccharide composition or film due to microbial activity. Examples include benzoates, such as methyl paraben.

In an embodiment, the composition further comprises an insecticide and/or a fungicide.

The composition of the present invention may also be present in the form of a concentrate which may be diluted before use with a suitable solvent, e.g. water, to a desired final concentration. A concentrate of the composition of the present invention has the advantage of facilitating and reducing costs for packaging and transportation of the product. In an embodiment, the concentrate of the composition of the present invention comprises a total concentration of polysaccharide in the range of 5-30% (w/v). In other embodiments the concentrate of the composition of the present invention comprises a total concentration of polysaccharide in the range of 10-30% (w/v) or 15-25% (w/v) based on dry weight of polysaccharide.

The inventive composition may advantageously be used for providing protection to surfaces against non-desired contamination, such as from so called graffiti, traffic pollution, bird droppings, etc. Therefore, in a second aspect thereof, the present invention provides the use of a polysaccharide composition as defined in any one of the preceding claims for protecting a substrate from contamination and facilitating removal of contamination therefrom.

Use of the inventive composition according to the second aspect of the invention allows the formation on substrates of protective films having sufficient thickness and stability towards water at room temperature with a single coating application, significantly reducing the costs for protecting surfaces.

In a third aspect thereof, the present invention provides a process for the preparation of a polysaccharide composition suitable for protection of surfaces comprising the steps:

a) mixing a first component (A) being a high molecular weight polysaccharide or a mixture of high molecular weight polysaccharides having an average molecular weight $M_w$ of at least 100 000, and being capable of forming a gel, and a second component (B) being a low molecular weight polysaccharide or a mixture of low molecular weight polysaccharides having an average molecular weight $M_w$ of about 400-75 000, and being capable of inhibiting gel formation of A, water, and optionally other components, wherein the weight ratio between A and B is in the range of from 5:1 to 1:20 based on polysaccharide dry weight, and the total concentration of A+B in the composition is in the range of 0.1-30% (w/v) based on polysaccharide dry weight, b) heating the mixture of a) to a temperature of at least 50° C. to dissolve components A and B and optionally other components in the water, and c) allowing the solution obtained in b) to cool down to room temperature.

The composition of the invention comprises an aqueous solution of a high molecular weight polysaccharide and a low molecular weight polysaccharide, wherein the high molecular weight polysaccharide may be present at a concentration at which it would normally form a gel at room temperature, but wherein gel formation is inhibited by the low molecular weight polysaccharide. Preparation of such solutions may be difficult since addition of the polysaccharides at room temperature may result in full or partial gel formation in the solution. This problem may be overcome by heating the mixture to a temperature at which all the polysaccharides in the solution are fully dissolved, and thereafter allowing the solution to cool down to room temperature. The present inventor has surprisingly found that this process allows the preparation of solutions with a high concentration of gel forming polysaccharides without the occurrence of gel formation when the solution is cooled down. It is believed that the reason for this is that gel formation is inhibited by the low molecular weight polysaccharides of the composition, although the disclosure of the present invention is not bound by any specific scientific theory. The present process may be particularly advantageous in the preparation of a concentrate of the composition of the invention since the polysaccharide concentration in such solutions is especially high.

In some cases in may be useful to heat the mixture to a higher temperature to facilitate dissolution of the polysaccharides. In an embodiment, the temperature of step b) is at least 80° C., such as for example about 95° C.

In a fourth aspect thereof, the present invention provides a process for protecting a substrate from contamination and facilitating removal of contamination therefrom, comprising the following steps:

a) providing a polysaccharide composition according to the present invention, b) applying the aqueous polysaccharide composition of a) to a substrate surface which is to be subjected to contamination.

c) allowing the applied composition to dry to form a protective film on said substrate surface.

The process as outlined above resides in principal in proceeding from a polysaccharide solution, to an intermediate gel and to a solid film.

This process makes use of the inherent advantageous features of the inventive composition in the formation of a protective film on a surface. The method according to the fourth aspect of the invention allows the formation on substrates of protective films having sufficient thickness and stability towards water at room temperature with few applications or even a single coating application, significantly reducing the costs for protecting surfaces. A further significant advantage in this aspect of the invention is that a high dry weight of polysaccharide in the composition reduces the drying time of the a formed coating, since the water content in the composition is low. This is especially advantageous where products comprising a polysaccharide film are prepared, and the drying of the coated or impregnated surface forms an integral step in the production process. The time and/or energy required for drying a coated or impregnated surface may be substantially reduced by the use of high concentration polysaccharide compositions made possible by the present disclosure.

In step a) of the process, a composition as described in the first aspect of the invention is provided. In step b) the composition is applied to a surface which is to be protected from contamination. Upon evaporation of the solvent from the composition applied to the surface, there will be formed a gel which is finally converted into a solid film. The resulting film resists dissolution by water at room temperature, since treatment with water only results in swelling of the film to a gel, unless the temperature is increased so that the gel will be dissolved.

The composition in the fourth aspect may comprise any feature mentioned herein in relation to the composition of the first aspect of the invention.

In a specific embodiment of the process of the invention, the application of the solution in step b) is performed in a single step. Single step application greatly reduces costs and effort associated with the protection of surfaces.

The thickness of the protective film formed according to the process of the present invention is important for the protective performance of the film. Generally, a film thickness of 1 µm may be sufficient for covering a smooth flat surface. However, most surfaces contain small or large irregularities, defects or pores, that may affect the film in such a way that the surface coverage of a thin film will not be satisfactory. Furthermore on surfaces exposed for example to an outdoor environment, the protective film may be eroded by rain, wind and particles, and by contact with passers by, such that the film thickness is decreased over time. It is therefore generally desired to have a thicker protective film. A thicker film also provides better protection, e.g. against graffiti, since it increases the time requires for a paint to diffuse through the protective film and reach the underlying substrate. Prior art compositions generally allow application of films having a thickness of about 10 µm or less in a single application step. Generally, at least two applications are required to obtain a sufficient film thickness, e.g. for graffiti protection. The present invention allows the application of films having a thickness of at least 20 µm in a single application step.

Therefore, in an embodiment of the process of the invention, the protective film resulting from step c) has a thickness of at least 10 µm, preferably at least 20 µm on said substrate surface.

In an embodiment of the process of the invention, the application of the solution in step b) is performed as a single application.

The protective film formed when the inventive composition is applied to a surface may preferably be removable by treatment with water at elevated temperature.

In an embodiment the process of the present invention further comprises the steps of:

d) treating the film formed in step c) with a liquid capable of re-dissolving and/or swelling the film, and e) removing contamination deposited on the film by complete or partial removal of the film from the substrate surface.

By complete or partial removal of the polysaccharide protective film from the surface which it is covers, any contamination deposited on the film after it was applied may also be removed.

The liquid capable of re-dissolving and/or swelling the film is preferably water based. The liquid may have an elevated temperature as compared to room temperature. In an embodiment, the temperature of the liquid is above 30° C. and preferably above 40° C. The temperature of the liquid may preferably be in the range of 40-100° C., such as 60-100° C. or 80-100° C. In a preferred embodiment, the liquid capable of re-dissolving and/or swelling the film is water at a temperature of about 40-60° C. In another embodiment, the temperature is in the range of 60-100° C.

In order to further facilitate removal of the film, the liquid may be applied at elevated pressure, for example using a high pressure cleaning apparatus. The pressure of the liquid may generally be in the range of 20-200 bars depending on the surface on which the protective film is deposited. In an embodiment, the pressure of the liquid is above 25 bars, such as above 50 bars or above 100 bars. In an embodiment, the pressure of the liquid is 50-80 bars. In another embodiment, the pressure of the liquid is 80-200 bars.

In a fifth aspect thereof, the present invention provides a substrate having a surface coated with a protective film comprising a first component (A) being a high molecular weight polysaccharide or a mixture of high molecular weight polysaccharides having an average molecular weight $M_w$ of at least 100 000, and being capable of forming a gel, and a second component (B) being a low molecular weight polysaccharide or a mixture of low molecular weight polysaccharides having an average molecular weight $M_w$ of about 400-75 000, and being capable of inhibiting gel formation of A, wherein the weight ratio between A and B is in the range of from 5:1 to 1:50 based on polysaccharide dry weight.

When a composition according to the present invention has been applied to a surface, water will evaporate from the film, resulting in an increase in the concentration of the polysaccharides in the film. When the polysaccharide concentration has reached a certain level, gel formation will occur, resulting in a significant increase in the stability of the film. Evaporation of water may then proceed until an equilibrium water content in the film has been reached. The protective film thus formed may have properties superior to the properties of the prior art, since coverage and adhesion of the film on the substrate can be optimized by tailoring the point at which gel formation occurs.

The substrate may preferably be coated with a protective film obtained by the above mentioned process.

In an embodiment, the substrate is selected from a group consisting of concrete, metal, stone, glass or wood. The substrate may also be a paint or varnish coated surface, such as e.g. a vehicle body.

If the substrate onto which the inventive composition is applied is porous, the composition may enter the pores of said substrate to form an impregnated substrate. The composition of the invention is especially advantageous in this respect, since it allows a high concentration of polysaccharides in solution, while maintaining a relatively low viscosity in the solution. Low viscosity is of course advantageous for allowing efficient impregnation of porous substrates.

The inventive composition may also be used for impregnating a porous cloth, tissue or weave, for example cellulose based, such as a paper, to obtain a product with improved resistance to water. The porous material may preferably be susceptible to biodegradation. Such a polysaccharide impregnated cloth, tissue or weave is useful as a degradable material, e.g. for covering the soil between desired plants in a plantation in order to reduce weed growth. The life time of the impregnated material may be extended by suspending the material above the ground such that the contact of the impregnated material with the soil is reduced or eliminated. When the material is no longer required, degradation may be accelerated by increasing the contact of the impregnated material with the soil. The inventive material thus provides an efficient and environmentally friendly alternative to herbicides. Another advantage of the impregnated material is that it allows water, e.g. from rain or artificial irrigation, to pass through the material. Many prior art materials are plastic based and do not allow passage of water. The amount of polysaccharide in the impregnated material may be varied within a wide range depending on the required properties of the impregnated material and the specific composition used. The impregnated material may comprise an amount of polysaccharide which is higher than or lower than or substantially equal to the amount of the porous material based on dry weight.

Thus, in a fifth aspect thereof, the present invention provides a porous material impregnated with a polysaccharide composition as defined hereinabove. The porous material may preferably be cellulose based. In an embodiment, the porous material is paper. In a more specific embodiment the impregnated material is a tissue paper impregnated with a composition according to the present invention wherein the high molecular weight polysaccharide component A comprises agar and guar gum, and the low molecular weight polysaccharide component B comprises a guar gum hydrolysate. In an embodiment, the dry weight ratio between the porous material and the polysaccharide in the impregnated material is in the range of from 10:1 to 1:10, preferably 10:1 to 1:2. In an more specific embodiment, the dry weight ratio between the porous material and the polysaccharide in the impregnated material is in the range of from 2:1 to 1:2. The composition used for impregnating the porous material may also further comprise a pigment, such as carbon black, to reduce the transparency to sunlight of the material.

In a sixth aspect thereof, the present invention provides the use of a composition according to the invention, further comprising a plasticizer and an insecticide and/or a fungicide, for protecting a plant or a plant part.

The composition is applied to a plant or plant part, e.g. by spraying or dipping. The composition then dries to form a protective film on the surface of said plant or plant part, wherein the formed film comprises an insecticide and/or a fungicide.

Preferably, the composition in this aspect of the invention comprises a high amount of a plasticizer, such as more than 25% (w/w) or more than 50% (w/w) based on the total weight of polysaccharide. In an embodiment, the composition in this aspect of the invention comprises at least 75% (w/w) of a plasticizer based on the total weight of polysaccharide. The plasticizer may for example be glycerol or a polyglycerol. Preferably the plasticizer is glycerol.

The high amount of plasticizer in the protective film allows the film to expand up to more than 20% without cracking. The expanded coating will on watering (artificially or by natural rain) absorb the water whereby the expansion pressure is alleviated. On drying the film will dry back to the new surface area of the growing plant part.

In order to provide for better adherence to plant parts (which sometimes has water repelling properties) polyimines or other polyamino compounds may be added to the composition.

The term "polysaccharide", as referred to herein, means a polymer molecule comprising at least three monosaccharide repeating units connected by glycoside linkages. The monosaccharide repeating units may be the same, i.e. a homopolysaccharide, or different, i.e. a heteropolysaccharide. The polymer chain may be straight or branched.

The term "low molecular weight polysaccharide", as referred to herein, means a polysaccharide molecule having an average molecular weight $M_w$ in the range of 400 to 75 000.

The term "high molecular weight polysaccharide", as referred to herein, means a polysaccharide molecule having an average molecular weight $M_w$ of at least 100 000. The average molecular weight $M_w$ of the high molecular weight polysaccharide may generally be in the range of the range of to 100 000 to 5 000 000.

The molecular weight $M_w$ used herein refers to the weight average molecular weight of the polysaccharides, which is well defined in the scientific literature. The unit of the molecular weight $M_w$ is g/mol.

The invention will in the following be further illustrated by non-limiting examples, wherein percentages are given in weight by volume unless otherwise indicated.

EXAMPLES

Example 1

Preparation of Hydrolysates

5% solutions of guar gum, agar and potato starch were prepared in aqueous hydrochloric acid (0.1 N). The solutions were heated at 100° C. for 2 hours. After cooling, the solutions were neutralized using aqueous sodium hydroxide (1.0 N). The solutions were then dialyzed against tap water for 18 hours (molecular weight cut-off was about 1000 for the dialysis tubing used). The solutions were then freeze dried. Analysis by gel permeation chromatography revealed that the molecular weights $M_w$ of the hydrolysates were about 10 000 g/mol.

Example 2

Inhibition of Gel Formation

The purpose of this experiment is to demonstrate that gel formation in solution is inhibited by the addition of low molecular weight polysaccharides.

a) To samples of a solution of 0.1% (w/v) of agar ($M_w$=100 000-1000 000) in water at 50° C. was added agar hydrolysate ($M_w$ about 10 000) prepared in accordance with example 1 to final concentrations of 0.1%, 0.2%, 0.3%, 0.4% and 0.5%. The samples were heated to 100° C. and then allowed to cool to 40° C. It was found that the sample with 0.1% agar gave a gel and that the addition of agar hydrolysate to the solution gradually weakened the gel and at a concentration of 0.3% or higher no gel was formed.

b) The above experiment was repeated using a solution of 0.2% (w/v) agar in water. No inhibition of the gel formation was observed at additions of agar hydrolysate up to 2.0%.

c) The experiment in a) was repeated using guar hydrolysate instead of agar hydrolysate and it was found that an addition of 1% or higher was needed to inhibit the gel formation.

d) The experiment in b) was repeated using guar hydrolysate instead of agar hydrolysate. No inhibition of the gel formation was observed at additions of guar hydrolysate up to 3%.

e) Experiments a) and b) were repeated using a starch hydrolysate. No inhibition of the gel formation was observed at additions of starch hydrolysate up to 3%.

Example 3

Protective Film Formation

To a mixture of agar (0.5 g, $M_w$=100 000-1 000 000), locust bean gum (20.0 g, $M_w$ above 100 000) and guar gum hydrolysate (20.0 g, $M_w$ about 10 000) was added ethanol (50 ml). To the slurry was added 1 liter of water under vigorous stirring. The resulting suspension was heated to 95° C. until a solution was formed. The solution was allowed to cool down to room temperature. Said solution was applied onto a concrete substrate (0.2 l/m$^2$). On drying the liquid phase turned into a gel before forming a film.

The resulting film was resistant to water (15° C.) but could be removed by the use of warm water (50° C.) at elevated pressure (50-80 bars). It was found that the film protected the concrete surface from pollutants such as bird droppings and graffiti (lacquer paints, felt pens etc.).

Example 4

Protective Film Formation

To a mixture of agar (1.0 g, $M_w$=100 000-1 000 000), guar gum (20.0 g, $M_w$ above 100 000) and guar gum hydrolysate (30.0 g, $M_w$ about 10 000) was added ethanol (50 ml). To the slurry was added 1 liter of water under vigorous stirring. The resulting suspension was heated to 95° C. until a solution was formed. The solution was allowed to cool down to room temperature. Said solution was applied onto a concrete substrate (0.2 l/m$^2$). On drying the liquid phase turned into a gel before forming a film.

The resulting film was resistant to water (15° C.) but could be removed by the use of warm water (50° C.) at elevated pressure (50-80 bars). It was found that the film protected the concrete surface from pollutants such as bird droppings and graffiti (lacquer paints, felt pens etc.).

Example 5

Protective Film Formation

To a mixture of agar (4.0 g, $M_w$=100 000-1 000 000) and guar gum hydrolysate (80 g, $M_w$ about 10 000) was added 1 liter of water under vigorous stirring. The resulting suspension was heated to 95° C. until a solution was formed. The solution was allowed to cool down to room temperature. Said solution was applied onto a concrete substrate (0.2 l/m$^2$). On drying the liquid phase turned into a gel before forming a film.

The resulting film was resistant to water (15° C.) but could be removed by the use of water (50° C.) at elevated pressure (50-80 bars). It was found that the film protected the concrete surface from pollutants such as bird droppings and graffiti (lacquer paints, felt pens etc.).

Example 6

Preparation of an Impregnated Substrate

To a mixture of agar (27 g, $M_w$=100 000-1 000 000), guar gum (10 g, $M_w$ above 100 000) and guar gum hydrolysate (410 g, $M_w$ about 10 000) was added 4.3 liters of water under vigorous stirring. The mixture was heated to 95° C. The solution was allowed to cool down to 70° C. and an antimicrobial agent (methylparaben), a surfactant (YES, Procter & Gamble (8 g) and glycerol (300 g) was added. The resulting mixture was allowed to cool to room temperature. To the resulting solution was added carbon black (2%, w/v) under high speed stirring.

TAD (through-air-dried) tissue (25 g/m$^2$, SCA Hygiene, Sweden) was sprayed with the above solution (0.2 liters/m$^2$). The resulting impregnated paper tissue was allowed to dry for 24 hours at room temperature.

The impregnated paper (black) with pre-punched plant holes was attached to a culturing cassette with 40 individual pots filled with soil. The cassette was seeded with spruce seeds. The seeds germinated and spruce plants were developed. The black paper prevented growth of mosses and weeds between the plants for more than 1 year.

Example 7

Plant Protection

To a mixture of agar (1.0 g, $M_w$=100 000-1 000 000), guar gum (20.0 g, $M_w$ above 100 000) and guar gum hydrolysate (30.0 g, $M_w$ about 10 000) was added ethanol (50 ml). To the slurry was added 1 liter of water under vigorous stirring. The resulting suspension was heated to 95° C. until a solution was formed. To the solution was then added glycerol (60 g). The solution was allowed to cool down to room temperature.

The resulting product was then diluted with water (1:10 v/v) and a cypermethrin formulation in vegetable oil (Cyper-Plus) was added, under vigorous stirring, to final concentration of 4% (v/v). The resulting emulsion was sprayed onto conifer plants (spruce).

After planting in an area heavily infested with large pine weevils (*Hylobius Abietis*) the plants were investigated for damages caused by the weevil after 1, 2 and 3 years, respectively. It was found that after 3 years more than 90% of the sprayed plants had survived whereas among unprotected control plants only 20% had survived.

The invention claimed is:

1. A polysaccharide composition for protection of surfaces comprising an aqueous solution of at least two components,
    the first component (A) being a high molecular weight polysaccharide or a mixture of high molecular weight polysaccharides having an average molecular weight Mw of at least 100 000, and being capable of forming a gel, and
    the second component (B) being a low molecular weight polysaccharide or a mixture of low molecular weight polysaccharides having an average molecular weight Mw of 400-75 000, and being capable of inhibiting gel formation in said composition,
    such that when said composition is applied onto a substrate surface and is allowed to dry, a film will be formed from the composition via at least partial gel formation,
    wherein the weight ratio between A and B is in the range of from 5:1 to 1:50 based on polysaccharide dry weight, and the total concentration of A+B in the composition is in the range of 0.1-30% (w/v) based on polysaccharide dry weight,
    wherein B is selected from the group consisting of guar gum, locust bean gum, and mixtures thereof.

2. The polysaccharide composition according to claim 1, wherein the weight ratio between A and B is in the range of from 2:1 to 1:20 based on polysaccharide dry weight.

3. The polysaccharide composition according to claim 2, wherein the weight ratio between A and B is in the range of from 2:1 to 1:10 based on polysaccharide dry weight.

4. The polysaccharide composition according to claim 1, wherein the total polysaccharide concentration in the solution is in the range of 1-20% (w/v) based on polysaccharide dry weight.

5. The polysaccharide composition according to claim 4, wherein the total polysaccharide concentration in the solution is in the range of 5-20% (w/v) based on polysaccharide dry weight.

6. The polysaccharide composition according to claim 1, wherein the composition is a concentrate, and the total concentration of polysaccharide is in the range of 15-25% (w/v) based on dry weight of polysaccharide.

7. The polysaccharide composition according to claim 1, wherein A is selected from the group consisting of algal, microbial and plant derived polysaccharides, and mixtures thereof.

8. The polysaccharide composition according to claim 7, wherein A is selected from the group consisting of agar, carrageenans, gellan gum, pectins or mixtures thereof.

9. The polysaccharide composition according to claim 7, wherein A further comprises a polysaccharide selected from the group consisting of guar gum, locust bean gum and mixtures thereof.

10. The polysaccharide composition according to claim 9, wherein A is a mixture of agar with guar gum and/or locust bean gum.

11. The polysaccharide composition according to claim 1, wherein B comprises a hydrolysate of a high molecular weight polysaccharide.

12. The polysaccharide composition according to claim 1, further comprising a third component (C), being a high molecular weight polysaccharide or a mixture of high molecular weight polysaccharides selected from the group consisting of starch, a starch derivative, cellulose and a cellulose derivative, wherein the total concentration of A+B+C in the composition is in the range of 0.1-30% (w/v) based on polysaccharide dry weight.

13. The polysaccharide composition according to claim 1, further comprising at least one additive selected from the group consisting of an anti-foaming agent, a plasticizer, a surfactant, and an antimicrobial agent.

14. A process for protecting a substrate from contamination and facilitating removal of contamination therefrom, comprising:
   a) providing the polysaccharide composition as defined in claim 1,
   b) applying the aqueous polysaccharide composition of a) to a substrate surface which is to be subjected to contamination,
   c) allowing the applied composition to dry to form a protective film on said substrate surface.

15. The process according to claim 14, wherein the application of the solution in step b) is performed as a single application.

16. The process according to claim 15, wherein the protective film resulting from step c) has a thickness of at least 20 μm on said substrate surface.

17. The process according to claim 14, further comprising:
   d) treating the film formed in step c) with a liquid capable of re-dissolving and/or swelling the film, and
   e) removing contamination deposited on the film by complete or partial removal of the film from the substrate surface.

18. A process for the preparation of a polysaccharide composition suitable for protection of surfaces comprising:
   a) mixing a first component (A) being a high molecular weight polysaccharide or a mixture of high molecular weight polysaccharides having an average molecular weight Mw of at least 100 000, and being capable of forming a gel, and a second component (B) being a low molecular weight polysaccharide or a mixture of low molecular weight polysaccharides having an average molecular weight Mw of about 400-75 000, and being capable of inhibiting gel formation of A, water, and optionally other components, such that when said composition is applied onto a substrate surface and is allowed to dry, a film will be formed from the composition via at least partial gel formation, wherein the weight ratio between A and B is in the range of from 5:1 to 1:50 based on polysaccharide dry weight, and the total concentration of A+B in the composition is in the range of 0.1-30% (w/v) based on polysaccharide dry weight, wherein B is selected from the group consisting of guar gum, locust bean gum, and mixtures thereof,
   b) heating the mixture of a) to a temperature of at least 80° C. to dissolve components A and B and optionally other components in the water, and
   c) allowing the solution obtained in b) to cool down to room temperature.

19. The process according to claim 18, wherein the temperature in step b) is at least 90° C.

20. A method of protecting a substrate from contamination and facilitating a removal of contamination therefrom, comprising:
   applying the polysaccharide composition as defined in claim 1 to the substrate to form a protective film on the substrate.

21. A substrate comprising:
   a surface coated with a protective film formed from the polysaccharide composition of claim 1.

22. A substrate according to claim 21, wherein the thickness of the protective film is at least 20 μm.

23. The substrate coated with a protective film according to claim 21, wherein the substrate is selected from the group consisting of concrete, metal, stone, glass or wood.

24. The substrate coated with a protective film according to claim 21, wherein the substrate is a porous cloth, tissue or weave impregnated with the composition.

25. The substrate coated with a protective film according to claim 21, wherein the substrate is paper.

26. A method of protecting a plant or a plant part, comprising:
   applying the polysaccharide composition according to claim 1 to the plant or the plant part to form a protective film on the plant or the plant part, the polysaccharide composition further comprising a plasticizer and an insecticide and/or a fungicide.

* * * * *